(12) United States Patent
Sasing

(10) Patent No.: US 7,306,606 B2
(45) Date of Patent: Dec. 11, 2007

(54) MULTI-AXIAL BONE SCREW MECHANISM

(75) Inventor: Jude L. Sasing, Quezon (PH)

(73) Assignee: Orthopaedic Innovations, Inc., Minneapolis, MN (US)

( * ) Notice: Subject to any disclaimer, the term of this patent is extended or adjusted under 35 U.S.C. 154(b) by 103 days.

(21) Appl. No.: 11/014,685

(22) Filed: Dec. 15, 2004

(65) Prior Publication Data
US 2006/0149232 A1 Jul. 6, 2006

(51) Int. Cl.
*A61B 17/58* (2006.01)
(52) U.S. Cl. ...................................................... 606/61
(58) Field of Classification Search ................... 606/61, 606/72–73
See application file for complete search history.

(56) References Cited

U.S. PATENT DOCUMENTS

| | | |
|---|---|---|
| 4,805,602 A | 2/1989 | Puno et al. |
| 5,360,431 A | 11/1994 | Puno et al. |
| 5,466,237 A | 11/1995 | Byrd, III et al. |
| 5,474,555 A | 12/1995 | Puno et al. |
| 5,496,321 A | 3/1996 | Puno et al. |
| 5,624,442 A | 4/1997 | Mellinger et al. |
| 6,063,090 A | 5/2000 | Schläpfer |
| RE37,665 E | 4/2002 | Ralph et al. |
| 6,443,953 B1 | 9/2002 | Perra et al. |
| 6,520,963 B1 * | 2/2003 | McKinley ..................... 606/61 |
| 6,626,908 B2 * | 9/2003 | Cooper et al. ................. 606/61 |
| 6,660,004 B2 * | 12/2003 | Barker et al. .................. 606/61 |
| 6,840,940 B2 | 1/2005 | Ralph et al. |
| 2002/0026193 A1 | 2/2002 | Barker et al. |
| 2002/0143341 A1 * | 10/2002 | Biedermann et al. ......... 606/73 |
| 2003/0100896 A1 * | 5/2003 | Biedermann et al. ......... 606/61 |
| 2004/0193160 A1 | 9/2004 | Richelsoph |

FOREIGN PATENT DOCUMENTS

| | | |
|---|---|---|
| EP | 1 210 914 | 6/2002 |
| WO | WO 95/35067 | 12/1995 |

* cited by examiner

*Primary Examiner*—Eduardo C. Robert
*Assistant Examiner*—Anitza M San Miguel
(74) *Attorney, Agent, or Firm*—Kagan Binder, PLLC

(57) ABSTRACT

A bone screw assembly including a coupling member with a lower surface and a channel formed by two arms extending from a base portion. The coupling member has a hole extending from the base portion of the channel to its lower surface. The assembly further includes a spacer having a top surface adjacent the base portion of the channel and a bottom surface generally opposite the top surface within the hole of the coupling member, and includes a hollow retaining ring within the hole of the coupling member, the retaining ring comprising an inner surface, an outer surface, a top surface spaced from the bottom surface of the spacer, and a slot extending from the inner surface of the ring to the outer surface of the ring. The assembly includes a bone screw having a head portion with an outer surface adjacent to the inner surface of the retaining ring.

20 Claims, 4 Drawing Sheets

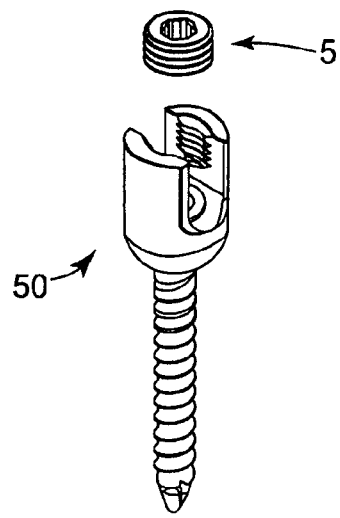
Fig. 1
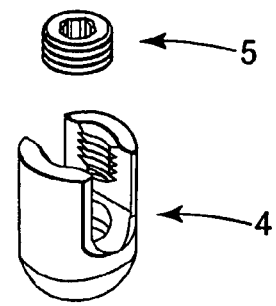
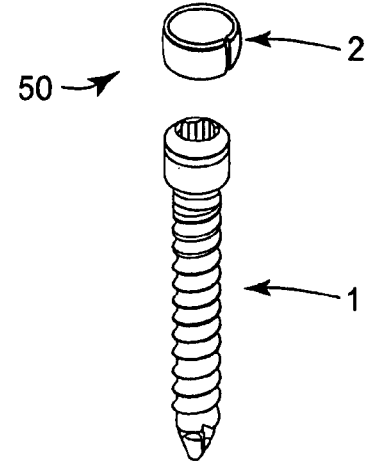
Fig. 2
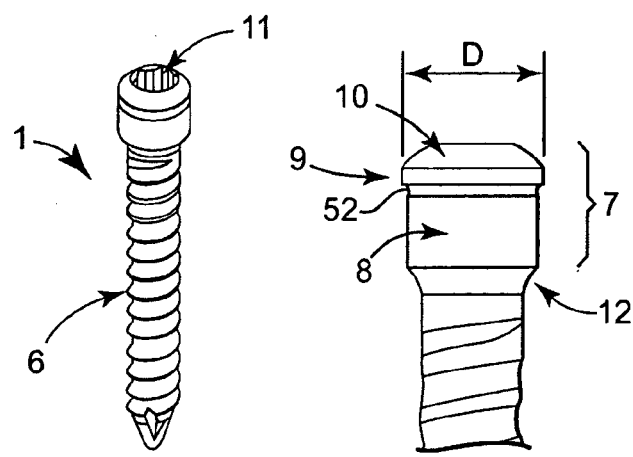
Fig. 3a   Fig. 3b

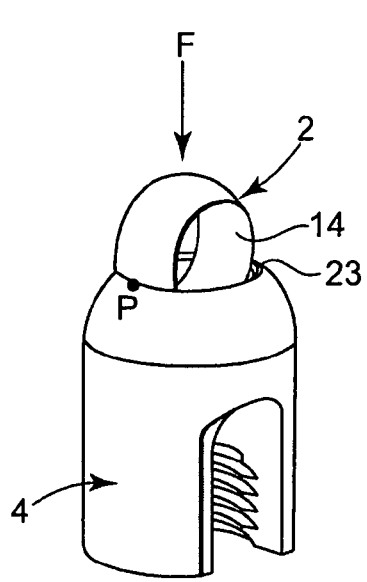
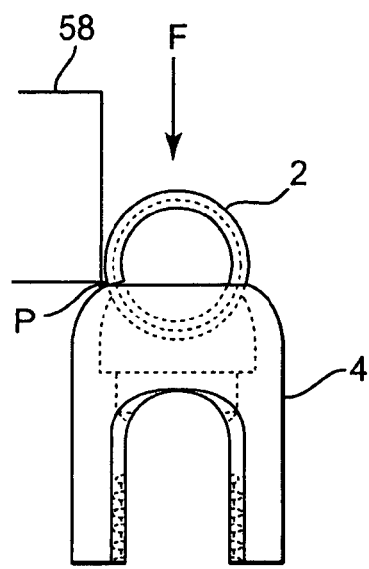
Fig. 7a        Fig. 7b
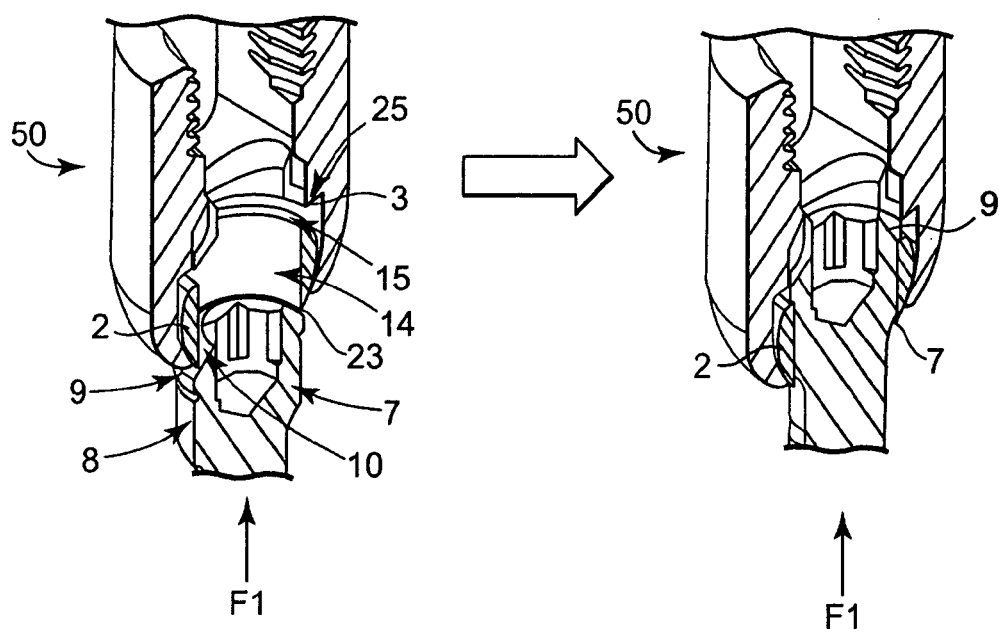
Fig. 8a        Fig. 8b

MULTI-AXIAL BONE SCREW MECHANISM

TECHNICAL FIELD

The present invention relates generally to devices for use in spinal surgery and methods of using such devices. More particularly, the present invention relates to multi-axial bone screw mechanisms for anchoring a vertebral body to a spinal fixation system as part of a surgical procedure.

BACKGROUND OF THE INVENTION

Surgically implanted systems, such as fixation devices and apparatuses, are commonly used to correct a variety of back structure problems, including those that occur as a result of trauma or improper development during growth. Generally, these systems correct such problems by providing a desired corrective spatial relationship between vertebral bodies. A typical spinal fixation system generally comprises a support rod or system of support rods that are secured along at least a portion of the spinal column intended to be immobilized by bone screws or hooks or other bone engaging components. Particular systems may include one or more fixation rods that are coupled to adjacent vertebra by attaching the rods to various anchoring devices, such as hooks, bolts, wires, or screws. Such bone anchors or devices may be directly connected to the support rods or may be connected indirectly by using medial/lateral connectors or other similar components. The bone screws, bone hooks, medial/lateral connectors, and/or related items that function to anchor the support rods to the bones are often collectively referred to as bone engaging hardware or implants.

Bone anchors such as screws and hooks are commonly utilized to facilitate segmental attachment of connective structures to the posterior surfaces of the spinal laminae. In a basic spinal fixation system, bone screws have a rod receiving opening extending through a head portion of each bone screw. The bone screws are typically secured through the pedicles and into the vertebral bodies at desired locations and a support rod is then extended through the opening in each bone screw. In particular, in order to accommodate connection to a spinal rod, many of these bone anchors are open-ended at an end distal from the end that is secured to a vertebra and have a yoke with a pair of upstanding arms that can receive a spinal rod in a channel formed between the arms. Because the rod connection portion of such bone anchors are open-ended, some type of fastener must be used in order to capture the rod or other structure as it is received within the open end of the anchor.

In order in order to fix the translational and rotational relationship of a support rod within the openings, various fastening techniques and devices can further be used to facilitate the securing of a spinal rod or rods to bone anchors of a spinal fixation system. For example, in one typical spinal fixation system, bone screws that have a rod receiving slot or opening in a head portion of the screw are implanted in predetermined vertebrae of the spine (adjacent vertebra, for example) and a spinal rod is then extended through the slot opening in each bone screw. The bones screws are then connected to the spinal rod by a setscrew or nut that engages the rod through or over a wall of the screw head. Tightening the setscrew or nut causes the spinal rod to be forced or clamped within the head of the bone screw thereby providing a holding force that attaches the spinal rod to the bone screw. The application of a pre-specified torque to the screw or nut provides a rigid construct for indefinite duration.

The fixation rods for a particular spinal fixation system are chosen according to a particular implantation site, and once installed, the fixation system holds the vertebral bodies in a desired spatial relationship, either until desired healing or spinal fusion has taken place, or for some longer period of time. For a spinal alignment correction with any of these systems that use a rod, the shapes of the support rods are utilized as the means to define and maintain the desired spinal curvature or vertebral alignment. Each rod is designed or selected to support a particular spine in a desired manner or to exert the desired corrective or stabilizing forces to the spine. Thus, each support rod can be bent or formed to a predetermined contour prior to positioning it in the rod-receiving opening of the bone screw. Alternatively, the support rods may be bent during the surgical procedure to accommodate the spinal correction or stabilization needed for each individual patient.

Other fixation systems have been developed that use medial/lateral connectors in association with bone screws to secure the support rods to the vertebra. The bone screws used in these systems typically include a threaded stud extending from the screw heads. The medial/lateral connectors include an arm and a head, and a rod receiving opening that extends through the head for connection to a support rod with a setscrew or other locking device. The arm of the connector includes an opening, such as a hole or slot that can receive the threaded stud of a bone screw. A fastener can then be used to attach the bone screw to the medial/lateral connector. This type of system is utilized in correcting spinal structural deformities or abnormalities is the same general manner as the fixation system above described wherein the support rods are shaped to define and maintain a desired spinal alignment.

With any of these systems that utilize a bone screw, it is common for the screw to pivot or otherwise move in at least one direction to achieve variable angular positions relative to the rod. In some cases, the screws are provided with the capability to move in three dimensions with respect to the rod in order to provide additional flexibility for positioning of the bone screw relative to the rod. These types of screws are often referred to as poly-axial or multi-axial screws.

Several types of multi-axial bone screw mechanisms have been developed and are available in the market. Generally, these are of two types that can be referred to as top-loaded and bottom-loaded systems. In top-loaded systems, a bone screw is assembled into a coupling member from the top, with the threaded portion inserted first and through the coupling member until the bone screw head engages the bottom portion of the cavity inside the coupling member. One disadvantage of these systems is that since the threaded portion of the bone screw must go through the coupling member, the dimensions of the coupling member must be able to accommodate the largest thread diameter of the bone screw. Typically, this results in a relatively large and bulky coupling member in a system that is desirably as small as possible.

In bottom-loaded systems, the bone screw is assembled into a coupling member from the bottom, which typically allows for a smaller coupling member since the screw member does not pass through the coupling member during assembly. However, one difficulty with bottom-loaded systems is preventing the head from being pushed out of the coupling member once it is inserted into the coupling member cavity. One design, which is disclosed in U.S. Pat. No. 6,660,004 to Barker et al., makes use of an internal retaining ring deployed inside a groove at the bottom of the coupling member. However, this design is limited in the amount of angulation between the bone screw and the coupling member. In order to maintain a desired level of strength for the grooved portion of the coupling member, a certain amount of material must be left at the bottom of the coupling member in order to support the retaining ring. This extra material impinges on the neck connecting the threaded portion to the head of the bone screw. In order to increase the angulation, the neck diameter must be reduced, which could weaken the bone screw. It is thus desirable to provide a bone screw system that allows for a higher degree of angulation while maintaining a sufficiently large neck diameter for strength of the screw.

SUMMARY OF THE INVENTION

In one aspect of this invention, a multi-axial bone screw is provided that has the capability to achieve a large range of variable angular positions while maintaining sufficient bone screw size and strength. More specifically, the present invention is directed to a multi-axial bone screw that can be securely attached to an elongated member such as a spinal fixation rod at different angles. It is composed generally of a bone screw, a spherical retaining ring, a spacer, a locking member, and a coupling member. The bone screw has a head with a shoulder that engages the spherical retaining ring such that the head can be pushed into the spherical retaining ring in one direction, but cannot be pushed out in the opposite direction. The coupling member has a slot to accommodate the spinal rod, and a cavity that connects to the top portion and to the bottom portion. The locking member is attached to the coupling member, and it pushes against the spinal rod when it is tightened to secure the rod within the slot. In one aspect of the invention, the bone screw is assembled such that the spacer, spherical retaining ring, and the head of the bone screw are inside the cavity of the coupling member. The spherical retaining ring allows the bone screw to pivot and be oriented at different angles relative to the coupling member. When the locking member is tightened, it pushes the spinal rod against the spacer. The spacer pushes against the head of the bone screw, which is attached to the spherical retaining ring. The spherical retaining ring is in turn pushed against the bottom portion of the cavity in the coupling member, locking the whole assembly.

In one particular embodiment of the invention, a bone screw assembly is provided which comprises a coupling member having a lower surface and a channel opposite the lower surface, the channel being formed by two arms extending from a base portion. The coupling member has a hole extending through the coupling member from the base portion of the channel to the lower surface of the coupling member. The assembly further includes a spacer within the hole of the coupling member, the spacer having a top surface adjacent to the base portion of the channel and a bottom surface generally opposite the top surface and also includes a hollow retaining ring within the hole of the coupling member, the retaining ring comprising an inner surface, an outer surface, a top surface spaced from the bottom surface of the spacer, and a slot extending from the inner surface of the ring to the outer surface of the ring. The assembly also includes a bone screw having a head portion with an outer surface adjacent to the inner surface of the retaining ring and a threaded portion extending from the head portion. The assembly may further include a locking member for attachment to the coupling member, wherein the locking member may be a setscrew or a nut, for example.

The present invention also includes a method of assembling a bone screw assembly, including the steps of providing a coupling member having a lower surface, a channel opposite the lower surface, and a hole through the coupling member from the channel to the lower surface, inserting a spacer having a top surface and a bottom surface into the hole through the lower surface of the coupling member so that the top surface of the spacer is adjacent to the channel, inserting a hollow retaining ring into the hole through the lower surface of the coupling member so that a top surface of the retaining ring is spaced from the bottom surface of the spacer, and inserting a bone screw comprising a threaded portion extending from a head portion into the hole through the lower surface of the coupling member so that a top portion of the head portion is adjacent to the bottom surface of the spacer and the entire threaded portion is external to the coupling member. The method may further include the steps of inserting an elongated rod into the channel of the coupling member and securing the rod in the channel by attaching a locking member to the coupling member.

BRIEF DESCRIPTION OF THE DRAWINGS

The present invention will be further explained with reference to the appended Figures, wherein like structure is referred to by like numerals throughout the several views, and wherein:

FIG. 1 is a partially exploded perspective view of a bone screw assembly of the present invention, including a setscrew that can be used to secure a rod to the bone screw assembly;

FIG. 2 is an exploded perspective view of the bone screw assembly of FIG. 1;

FIG. 3a is a perspective view of the bone screw of FIG. 2, and FIG. 3b is an enlarged view of the head portion of the bone screw;

FIG. 7a is a perspective view illustrating the assembly of the retaining ring and coupling member of FIG. 1, including a desired directional force for assembly, and FIG. 7b is a front view of this assembly with the interior portion of the assembly in phantom lines;

FIG. 8a is a cross-sectional perspective view of the bone screw of FIGS. 1-3 positioned for assembly within the coupling member of FIGS. 1 and 2, including a desired directional force for assembly, and FIG. 8b is a cross-sectional perspective view of the assembly after the bone screw has been inserted into the coupling member.

DETAILED DESCRIPTION OF THE PREFERRED EMBODIMENTS

Figure 4:
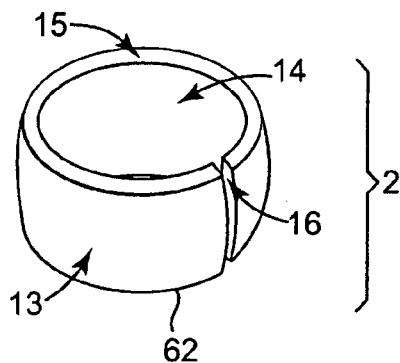
FIG. 4 is a perspective view of the spherical retaining ring of FIG. 1.

The present invention is related to a multi-axial bone screw assembly that can be securely attached to another component or member at a wide variety of different angles. In a particular preferred use, the bone screw assembly of the present invention is used primarily for spinal applications where a pedicle screw has to be securely attached to a spinal rod at varying angles, such as to provide a desired corrective spatial relationship between vertebral bodies. However, it is understood that the bone screw assembly of the present invention may instead be used for attachment to other components and/or in systems that are related to correction of other physical problems that may or may not be related to the spine.

Referring now to the Figures, wherein the components are labeled with like numerals throughout the several Figures, and initially to FIGS. 1 and 2, one preferred configuration of a bone screw assembly 50 is illustrated, which generally includes a bone screw 1, a spherical retaining ring 2, a spacer 3, a coupling member 4, and a setscrew 5. These components are designed and assembled in such a way that bone screw 1 can be oriented at various angles relative to an elongated member such as a spinal rod and locked securely relative to the same elongated member.

With further reference to FIGS. 3a and 3b, bone screw 1 includes a threaded portion 6 for anchoring into bone, such as the pedicle portion of a vertebral body. It has a head portion 7 having an outer cylindrical surface 8, a shoulder 9, a spherical, angled, or convex surface 10 at the top, and a driving socket 11 for accepting a driving tool such as a hexagonal screwdriver. The head portion further includes a recessed channel 52 that extends around the circumference of the head portion 7 between the outer cylindrical surface 8 and the shoulder 9. The head portion 7 may instead be configured differently than that shown, such as with a spherical surface at the top that is shaped or sized differently than shown (e.g., a head portion 7 that has a different taper or shape between the shoulder 9 and the driving socket 11 at surface 10), with additional or different contours and transition areas, as desired. Further, the driving socket 11 may instead be an opening that is shaped differently than a hexagon, such as a slot or square, or may instead include a protruding element that can be manipulated by a tool. Any alternative configurations of the head portion 7 should desirably be designed for compatibility with the inside of the coupling member 4 and retaining ring 2, as will be described in further detail below. That is, any variations of one of the components described herein should include a corresponding variation of any mating or connecting components to achieve the specific relationships between the elements of the invention as described.

The bone screw 1 further includes a tapered neck portion 12 that extends between the head portion 7 and the threaded portion 6, where this neck portion 12 preferably provides a relatively smooth transition between the head portion 7 and the threaded portion 6. It is preferable that the transition between these parts of the bone screw does not include sharp transitions that may cause areas of stress concentrations and thus the neck portion is preferably configured to minimize the possibility of fatigue or other stresses on the bone screw 1.

Referring now to FIG. 4, spherical retaining ring 2 preferably includes a curved or spherical outer surface 13, a cylindrical inner surface 14, and a flat surface 15 extending between the outer surface 13 and the inner surface 14 and an edge 62 generally opposite the flat surface 15. As shown, the outer surface 13, which is also referred to herein as the spherical outer surface 13, is generally convex in shape. The shape of this outer surface 13 may be a portion of a full sphere as it would be truncated at the flat surface 15 and at the edge 62. In this case, it is possible that the retaining ring 2 is machined from a hollow sphere, where the sphere is cut on two ends to provide the flat surface 15 and the edge 62. Alternatively, the retaining ring 2 can be manufactured by molding or some other method that provides the desired outer convex shape of the surface 13. In another alternative, the convex shape of the outer surface 13 may have a curve that does not comprise a portion of a sphere, but could instead be a portion of an ellipse or another symmetrical or nonsymmetrical shape, as desired. In accordance with the invention, the inner surface 14 is preferably relatively smooth and is sized to accept the outer cylindrical surface 8 of the head portion 7 of the bone screw 1. The retaining ring 2 also includes a slot or gap 16 that extends through the wall of the retaining ring 2 from the outer surface 13 to the inner surface 14. The size of the slot or gap 16 is chosen to allow the ring 2 to flex or deform at least slightly, much like other standard retaining rings.

Figures 5A, 5B:
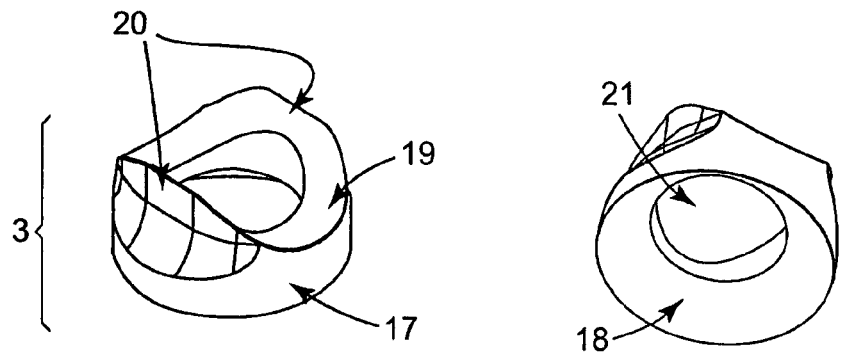
FIG. 5a is a perspective top view of the spacer of FIG. 1.
FIG. 5b is a perspective bottom view of that spacer.

FIGS. 5a and 5b illustrate in detail the specific features of one preferred spacer 3 of the present invention. In particular, the spacer 3 has an outer cylindrical surface 17, and a spherical or concave surface 18 that generally matches surface 10 of bone screw head 7. Spacer 3 further includes a generally U-shaped channel 19, two substantially parallel flat surfaces 20 on opposite sides of the channel 19, and a through-hole 21 that extends through the spacer 3 from the spherical surface 18 to the channel 19. The specific shapes and dimensions of the various surfaces of the spacer 3 can vary considerably, but are preferably selected to mate or match with corresponding surfaces on other components in a bone screw assembly, such as the retaining ring 2 and the inside of the coupling member 4.

Figure 6A:
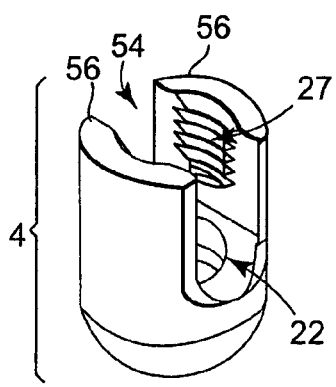
FIG. 6a is a perspective view of the coupling member of FIG. 1.
Figure 6B:
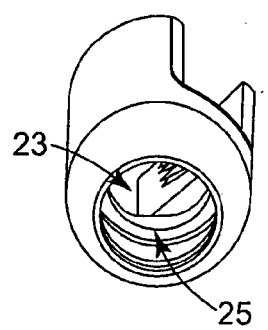
FIG. 6b is a bottom perspective view of that coupling member.
Figure 6C:
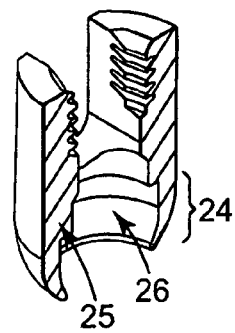
FIG. 6c is a cross-sectional perspective view of that coupling member.
Figure 9A:
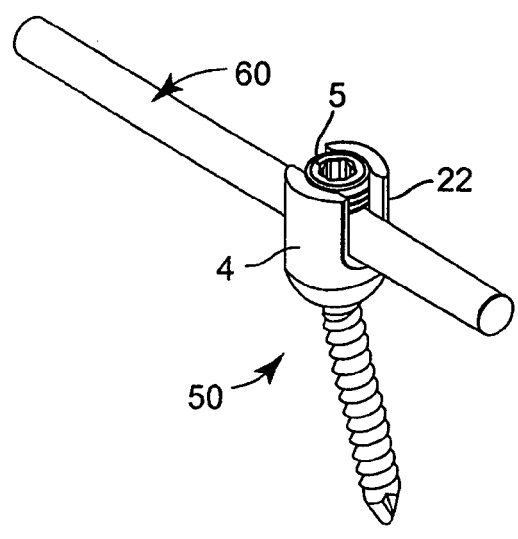
FIGS. 9a and 9b are a perspective view and a front view, respectively, of the bone screw assembly of the present invention including a spinal rod secured into the cavity of the coupling member.
Figure 9B:
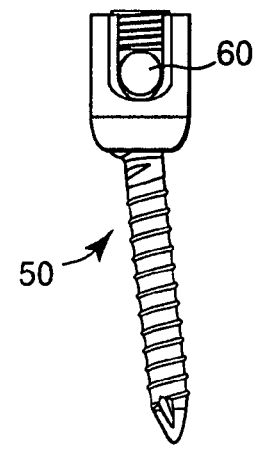

A preferred embodiment of coupling member 4 is illustrated in several views in FIGS. 6a, 6b, and 6c. Coupling member 4 includes a generally U-shaped channel 54 formed between two extending arms 56 that preferably extend parallel to each other on opposite sides of the channel 54. Coupling member 4 further includes a slot 22 through the area between the extending arms 56 in the channel 54, a hole 23 through the bottom surface of the coupling member 4, and a cavity 24 that extends between slot 22 and hole 23. Cavity 24 further includes a flat surface 25 and a bottom surface 26, which is preferably contoured to be generally concave. Coupling member 4 also includes a means of attaching a locking member in order to secure an elongated rod or other component within the channel 54 of the member 4. In the preferred embodiment, this means of attaching a locking member includes internal threads 27. The locking member in the preferred embodiment is a setscrew 5 (see FIGS. 1 and 2) that matches the internal threads 27. The component designs used to lock a component within the channel 54 can vary widely and are considered to be within the scope of the present invention. For example, the extending arms 56 may instead include threads on their outer surfaces such that an internally threaded setscrew or other threaded component may be used for locking purposes.

In one preferred configuration of the bone screw assembly 50 of the present invention, the spherical retaining ring 2 will be positioned inside the cavity 24 of coupling member 4. Bone screw head 7 is then passed through hole 23 of coupling member 4 from the bottom of coupling member 4 opposite the channel 54, where it can engage with spherical retaining ring 2 inside cavity 24. Spherical retaining ring 2 then forms a rotating "ball and socket" pair within bottom surface 26 of cavity 24, as will be described in further detail below.

Although the bone screw assembly 50 may be assembled in a number of ways, one preferred method of assembly includes first pressing spacer 3 into the cavity 24 of coupling member 4 through the hole 23. Outer cylindrical surface 17 of spacer 3 preferably has a diameter that is slightly smaller than the diameter of hole 23 at the bottom of coupling member 4, but larger than the width of slot 22 of coupling member 4. Spacer 3 is thus small enough to pass through hole 23 at the bottom of coupling member 4, but is too large to pass through slot 22 and into the channel 54 at the top. The distance between flat surfaces 20 of spacer 3 is slightly less than the width of slot 22 in coupling member 4, so that spacer 3 can partially go through slot 22. When spacer 3 is partially through slot 22, flat surfaces 20 engage the sides of slot 22 so that the orientation of spacer 3 relative to coupling member 4 is fixed and channel 19 in spacer 3 preferably protrudes at least slightly from slot 22 and is preferably generally parallel to channel 54.

Spherical retaining ring 2 is then pressed into cavity 24 through hole 23 at the bottom of coupling member 4. The diameter of spherical outer surface 13 of spherical retaining ring 2 is at least slightly larger than the inside diameter of hole 23 in coupling member 4. Preferably, the difference in diameter between the outer surface 13 and the hole 23 is small so that the fit between the retaining ring 2 and the coupling member 4 will be relatively tight or secure when the retaining ring 2 is in place. Slot 16 in spherical retaining ring 2 allows spherical retaining ring 2 to be compressed or deformed in such a way as to allow it to fit through hole 23, then to expand to a larger diameter within the cavity 24 when in position and the compressive forces are reduced. Thus, the retaining ring 2 is preferably made of a material that has enough elasticity that is does not deform permanently when compressed to fit into the hole 23. Rather, the material from which the retaining ring 2 is made should preferably expand back to its uncompressed state when the compressive force is removed from it. In addition, it is preferable that the material from which the retaining ring 2 is made is relatively stiff, yet flexible enough to allow its deformation under a reasonable amount of pressure.

There are at least two ways to make spherical retaining ring 2 pass through hole 23 of coupling member 4. In one method, the spherical retaining ring 2 can be compressed until its diameter becomes less than the diameter of hole 23, much like deploying a standard internal retaining ring. This method would require a substantially large width of slot 16 in order to accommodate for the deformation required for retaining ring 2 to fit into hole 23. However, a large slot 16 would significantly reduce the contact area between spherical surface 13 and bottom surface 26 of cavity 24 once the retaining ring is in place inside cavity 24, which could in turn affect the locking security of the assembly. Thus, if this assembly method is used, the size of the slot 16 should preferably be selected to be as small as possible to maximize the contact area once the retaining ring 2 is positioned within the coupling member 4, but large enough to allow for the necessary deformation of the ring for insertion through the hole 23.

Another method of assembling spherical retaining ring 2 within coupling member 4 through hole 23 is illustrated in FIGS. 7a and 7b. In this method, spherical retaining ring 2 is oriented such that the axis of cylindrical inner surface 14 of retaining ring 2 is perpendicular to the axis of hole 23. One side of slot 16 in spherical retaining ring 2 is abutted against the edge of hole 23 at point P that is preferably at the approximate centerline of the retaining ring 2. A force F is then applied in the direction shown (i.e., at least a portion of the force is parallel to the axis of hole 23, although the directional force may also have force vectors in at least one additional direction) to push spherical retaining ring 2 into hole 23 while the abutting side of slot 16 pivots about point P, until spherical retaining ring 2 slips through hole 23 and goes into cavity 24. A constraining fixture 58 may be used to keep the abutting side of slot 16 from moving, and force it to pivot about point P. Once spherical retaining ring 2 is inside cavity 24, it can be realigned such that the axis of cylindrical inner surface 14 is parallel to the axis of hole 23. Using this method, only a narrow width of slot 16 is required in order for spherical retaining ring 2 to pass through hole 23 since substantial compression of the ring 2 is not required. This assembly method allows for a larger contact area between spherical outer surface 13 of retaining ring 2 and bottom surface 26 of cavity 24, which can provide improved locking security of the assembly.

Another variation of the preferred embodiment is the use of a superelastic alloy such as Nitinol (nickel-titanium alloy) as the material for spherical retaining ring 2. By using a superelastic alloy, the width of slot 16 could be kept to a minimum while the spherical retaining ring 2 can be inserted into cavity 24 without using the method illustrated in FIGS. 7a and 7b. This can be accomplished by compressing spherical retaining ring 2 such as is normally done for an internal retaining ring, but to a point that spherical retaining ring 2 elongates or becomes oval until it can be slipped through hole 23. After passing through hole 23, spherical retaining ring 2 can return to its original shape by virtue of the superelastic nature of its material.

Referring now to FIGS. 3b, 8a, and 8b, one preferred method of assembling the bone screw 1 into the bone screw assembly 50 is illustrated. In particular, the shoulder 9 has an outer diameter D that is slightly smaller than the diameter of hole 23 so that it can easily pass through hole 23 and into cavity 24. The diameter D of shoulder 9 is preferably larger than the diameter of cylindrical inner surface 14 of spherical retaining ring 2 when the ring 2 is in its relaxed state. That is, once the retaining ring 2 is positioned within the coupling member 4 as shown in FIG. 8a as described above, the retaining ring 2 should be in a state of equilibrium with no compressive or expansive forces being exerted upon it. When bone screw head 7 is pushed into the center of spherical retaining ring 2 as shown in FIGS. 8a and 8b, flat surface 15 of spherical retaining ring 2 abuts against flat surface 25 of cavity 24. Pushing bone screw head 7 further into the opening (in the direction of the arrow F1) causes spherical surface 10 to force spherical retaining ring 2 open at least slightly at the slot 16 until shoulder 9 of bone screw head 7 can pass through cylindrical surface 14 of spherical retaining ring 2. Cavity 24 of coupling member 4 is made large enough to accommodate this additional width of the spherical retaining ring 2 when it is spread open at least slightly by the bone screw head 7. Thus, the slot 16 in the retaining ring 2 increases the adaptability of the ring 2 both as it is compressed for insertion into the coupling member 4, as described above relative to FIGS. 7a and 7b, and also as it is expanded for insertion of the bone screw head 7 into the retaining ring 2 when assembling the bone screw assembly 50. Thus, it is preferable that the material selected for the retaining ring 2 has a memory and is elastically deformable both in compression and expansion so that it is not permanently deformed by either the process of inserting the ring 2 into the hole 23 or by the process of inserting the bone screw head 7 through its cylindrical surface 14.

Once shoulder 9 moves beyond the cylindrical surface 14, spherical retaining ring 2 collapses back toward the bone screw head 7 so that cylindrical surface 14 closes around cylindrical surface 8 of bone screw head 7. Preferably, the shoulder 9 abuts against the flat surface 15 of spherical retaining ring 2 so that bone screw head 7 cannot be pushed out of spherical retaining ring 2 in the direction opposite to the direction when it was pushed into spherical retaining ring 2 as discussed above. Further, the flat surface 15 at the top of the retaining ring 2 preferably at least partially protrudes or extends into the recessed channel 52, which helps to keep the bone screw 1 in place with the assembly 50. Since the diameter of spherical outer surface 13 of spherical retaining ring 2 is larger than the diameter of hole 23 of coupling member 4, bone screw 1 cannot be pulled out of coupling member 4, and spherical surface 13 of spherical retaining ring 2 articulates with bottom surface 26 of cavity 24 to form a "ball and socket" joint. This allows bone screw 1 to be oriented at different angles relative to coupling member 4.

One method of using the completed bone screw assembly of the present invention is generally applied in surgery as follows. A spinal rod 60 is selected to correct or maintain a certain relationship of adjacent vertebral bodies within a patient. As discussed above, this rod way be bent on site for a particular patient, or may be selected from available pre-bent rods. In either case, threaded portion 6 of bone screw 1 is threaded into bone, suet as the pedicle portion of a vertebral body, using a driving instrument such as a screwdriver attached to driving socket 11. Coupling member 4 is then angulated relative to bone screw 1 as required to align properly with a spinal rod in the orientation in which the rod is to be positioned within the patient. Spinal rod 60 is then placed in channel 54 of coupling member 4. Spinal rod 60 also sits on channel 19 of spacer 3 since channel 19 is generally protruding from the surfaces of the slot 22. Setscrew 5 is then positioned within the internal threads 27 of the extending arms 56 and rotated to move the setscrew 5 toward the rod 60. As setscrew 5 is tightened, it pushes spinal rod 60 against channel 19 of spacer 3, while spherical surface 18 of spacer 3 pushes against spherical surface 10 of bone screw head 7. At the same time, shoulder 9 of bone screw head 7 pushes against flat surface 15 of spherical retaining ring 2, which pushes spherical surface 13 against bottom surface 26 of cavity 24, thereby locking the whole assembly together. As spherical surface 13 is pushed against bottom surface 26, the contact force between spherical surface 13 and bottom surface 26 forces spherical retaining ring 2 to close further on bone screw head 7, further preventing bone screw head 7 from being pushed out of spherical retaining ring 2.

Other alternatives to the preferred embodiment described above would include variations in the locking member. As described above, the locking member 5 in the bone screw assembly 50 can be a setscrew. However, this locking member could be replaced by other elements that could impart a compressive force on the spinal rod, such as a nut or an unthreaded fastener that is pressed over the arms of the coupling member. Spacer 3 in the preferred embodiment incorporates a U-shaped channel 19. An alternative to this design would be a V-shaped channel. Channel 19 may also be omitted altogether, although this could reduce the stability of the assembly. Finally, even though the application of the present invention is described for a bone screw such as a pedicle screw, the same mechanism that allows for the angulation of the bone screw relative to an elongated member can be used for other bone-anchoring methods such as a hook. In this case, a hook-shaped feature would replace threaded portion 6 of bone screw 1, while the other elements of the present invention would remain essentially the same.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A bone screw assembly comprising:
   a coupling member comprising a lower surface and a channel opposite the lower surface, the channel being formed by two arms extending from a base portion;
   a hole extending through the coupling member from the base portion of the channel to the lower surface of the coupling member;
   a spacer within the hole of the coupling member, the spacer having a top surface adjacent to the base portion of the channel and a bottom surface generally opposite the top surface;
   a hollow retaining ring within the hole of the coupling member, the retaining ring comprising an inner surface, an outer surface, a top surface spaced from the bottom surface of the spacer, and a slot extending from the inner surface of the ring to the outer surface of the ring; and
   a bone screw comprising:
   a head portion having a top surface, an outer surface adjacent to the inner surface of the retaining ring, and a recessed channel extending around the periphery of the head portion and spaced from the top surface of the head portion; and
   a threaded portion extending from the head portion;
   wherein the top surface of the retaining ring at least partially extends into the recessed channel of the bone screw head portion.

2. The bone screw assembly of claim 1, wherein the bottom surface of the spacer extends generally from the hole in the base portion of the channel toward a center axis of the bone screw assembly.

3. The bone screw assembly of claim 1, wherein the retaining ring is pivotable within the hole of the coupling member.

4. The bone screw assembly of claim 3, wherein the retaining ring is pivotable about at least two axes of rotation.

5. The bone screw assembly of claim 3, wherein the bone screw is rotatable with the retaining ring relative to the hole of the coupling member.

6. The bone screw assembly of claim 1, wherein the entire threaded portion of the bone screw is external to the coupling member.

7. The bone screw assembly of claim 1, wherein the head portion of the bone screw is adjacent to the bottom surface of the spacer.

8. The bone screw assembly of claim 7, wherein the bottom surface of the spacer is generally concave and wherein the head portion of the bone screw comprises a generally convex portion that is adjacent to the bottom surface of the spacer.

9. The bone screw assembly of claim 1, further comprising a locking member for attachment to the coupling member.

10. The bone screw assembly of claim 9, wherein the locking member is a setscrew.

11. The bone screw of claim 1, in combination with an elongated rod extending through the channel of the coupling member.

12. The combination of claim 11, further comprising a locking member positioned for securing the rod within the channel.

13. The bone screw assembly of claim 1, wherein the retaining ring is compressible to decrease the width of the slot and the outer diameter of the retaining ring.

14. The bone screw assembly of claim 1, wherein the outer surface of the retaining ring in a relaxed condition has a diameter that is larger than an inner diameter of the hole in the coupling member and wherein the outer surface of the retaining ring in a compressed condition has a diameter that is less than the inner diameter of the hole in the coupling member.

15. The bone fixation system of claim 1, wherein the retaining ring is rotatable within the hole of the coupling member.

16. A bone fixation system comprising:
  a coupling member comprising a lower surface and a channel opposite the lower surface, the channel being formed by two arms extending from a base portion;
  a hole extending through the coupling member from the base portion of the channel to the lower surface of the coupling member;
  a spacer within the hole of the coupling member, the spacer having a top surface adjacent to the base portion of the channel and a bottom surface generally opposite the top surface;
  a hollow retaining ring within the hole of the coupling member, the retaining ring comprising an inner surface, an outer surface, a top surface spaced from the bottom surface of the spacer, and a slot extending from the inner surface of the ring to the outer surface of the ring;
  a bone screw comprising:
  a head portion having a top surface, an outer surface adjacent to the inner surface of the retaining ring, and a recessed channel extending round the periphery of the head portion and spaced from the top surface of the head portion; and
  a threaded portion extending from the head portion;
  wherein the top surface of the retaining ring at least partially extends into the recessed channel of the bone screw head portion;
    an elongated rod extending through the channel of the coupling member; and
  a locking member positioned for securing the rod within the channel of the coupling member.

17. A method of assembling a bone screw assembly comprising the steps of:
  providing a coupling member having a lower surface, a channel opposite the lower surface, a hole through the coupling member from the channel to the lower surface, and a coupling member axis extending through the coupling member hole;
  inserting a spacer having a top surface and a bottom surface into the hole through the lower surface of the coupling member so that the top surface of the spacer is adjacent to the channel;
  providing a hollow retaining ring comprising an inner surface defining a retaining ring hole, an outer surface, a slot extending from the inner surface of the ring to the outer surface of the ring, and a retaining ring axis extending through the retaining ring hole;
  orienting the retaining ring with the retaining ring axis generally perpendicular to the coupling member axis;
  inserting the hollow retaining ring into the coupling member hole through the lower surface of the coupling member by applying a force to the retaining ring along the coupling member axis; and
  inserting a bone screw comprising a threaded portion extending from a head portion into the coupling member hole through the lower surface of the coupling member so that a top portion of the head portion is adjacent to the bottom surface of the spacer and the entire threaded portion is external to the coupling member.

18. The method of claim 17, further comprising the steps of inserting an elongated rod into the channel of the coupling member and securing the rod in the channel by attaching a locking member to the coupling member.

19. The method of claim 17, wherein prior to the step of inserting the retaining ring into the coupling member hole, the method further comprises the step of positioning the retaining ring so that one side of the slot of the retaining ring is abutted against an edge of the coupling member hole.

20. The method of claim 17, further comprising the step of rotating the retaining ring within the coupling member so that the retaining ring axis is parallel to the coupling member axis and so that a top surface of the retaining ring is spaced from the bottom surface of the spacer.

* * * * *

UNITED STATES PATENT AND TRADEMARK OFFICE
CERTIFICATE OF CORRECTION

PATENT NO. : 7,306,606 B2  Page 1 of 1
APPLICATION NO. : 11/014685
DATED : December 11, 2007
INVENTOR(S) : Jude L. Sasing It is certified that error appears in the above-identified patent and that said Letters Patent is hereby corrected as shown below:

On the Title Page, Item (75)
Inventor data, please delete "Quezon (PH)" and insert in place thereof,
--Quezon City (PH)--.

On the Title Page, Item (73)
Assignee data, please delete "Orthopaedic Innovations, Inc., Minneapolis, MN (US) and insert in place thereof, --Orthopaedic International, Inc., Cabuyao, Laguna 4025, Philippines--.

Column 9,
Line 21, please delete "suet" and insert in place thereof, --such--.

Column 11,
Claim 16, Line 39, delete "round" and insert in place thereof, --around--.

Signed and Sealed this

Seventeenth Day of June, 2008

JON W. DUDAS
*Director of the United States Patent and Trademark Office*